(12) United States Patent
Abrevaya et al.

(10) Patent No.: US 8,304,593 B2
(45) Date of Patent: *Nov. 6, 2012

(54) HYDROCARBON CONVERSION USING AN IMPROVED MOLECULAR SIEVE

(75) Inventors: Hayim Abrevaya, Kenilworth, IL (US); Julio C. Marte, Carol Stream, IL (US); Stephen T. Wilson, Libertyville, IL (US); Susan C. Koster, Carpentersville, IL (US); John E. Bauer, LaGrange Park, IL (US); Wharton Sinkler, Des Plaines, IL (US); Ben A. Wilson, Algonquin, IL (US); Lance L. Jacobsen, Lake Zurich, IL (US)

(73) Assignee: UOP LLC, Des Plaines, IL (US)

( * ) Notice: Subject to any disclaimer, the term of this patent is extended or adjusted under 35 U.S.C. 154(b) by 660 days.

This patent is subject to a terminal disclaimer.

(21) Appl. No.: 12/365,536

(22) Filed: Feb. 4, 2009

(65) Prior Publication Data
US 2010/0152511 A1    Jun. 17, 2010

Related U.S. Application Data

(60) Provisional application No. 61/138,242, filed on Dec. 17, 2008.

(51) Int. Cl.
*C07C 5/22* (2006.01)

(52) U.S. Cl. ......... 585/477; 585/480; 585/481; 585/482

(58) Field of Classification Search .................. 585/477, 585/480, 481, 482
See application file for complete search history.

(56) References Cited

U.S. PATENT DOCUMENTS

| | | | |
|---|---|---|---|
| 4,758,419 A | | 7/1988 | Lok et al. |
| 5,240,891 A | * | 8/1993 | Patton et al. ..................... 502/66 |
| 5,276,236 A | * | 1/1994 | Patton et al. .................. 585/482 |
| 5,434,326 A | * | 7/1995 | Gajda et al. ................... 585/467 |
| 5,478,787 A | | 12/1995 | Dandekar et al. |
| 6,660,896 B1 | | 12/2003 | Buchanan et al. |
| 6,797,849 B2 | | 9/2004 | McMinn et al. |
| 7,368,620 B2 | | 5/2008 | Zhou et al. |
| 2007/0004947 A1 | * | 1/2007 | Zhou et al. ..................... 585/481 |

OTHER PUBLICATIONS

U.S. Appl. No. 12/365,518, filed Feb. 4, 2009, Abrevaya el al.
U.S. Appl. No. 12/365,545, filed Feb. 2, 2009, Abrevaya el al.
U.S. Appl. No. 12/365,584, filed Feb. 4, 2009, Abrevaya el al.

* cited by examiner

*Primary Examiner* — Elizabeth Wood
(74) *Attorney, Agent, or Firm* — Mark R Willis

(57) ABSTRACT

The present invention comprises a hydrocarbon-conversion process using an improved MgAPSO-31 molecular sieve which demonstrates a favorable combination of conversion and selectivity in aromatics conversion. The sieve has a specific combination of crystal configuration, being limited in diameter and length, specified crystallinity as measured by an X-Ray Diffraction Index (XRDI), and a narrow range of magnesium content.

16 Claims, 3 Drawing Sheets

HYDROCARBON CONVERSION USING AN IMPROVED MOLECULAR SIEVE

FIELD OF THE INVENTION

This invention relates to an improved molecular sieve and its use for the conversion of hydrocarbons. More specifically, the invention concerns a magnesium-containing non-zeolitic molecular sieve which has a narrowly defined composition and is particularly useful for isomerization.

GENERAL BACKGROUND AND KNOWN ART

Molecular sieves, most commonly zeolites, have a long history of use in catalysts for hydrocarbon conversion. More recently, a class of useful non-zeolitic molecular sieves containing framework tetrahedral units ($TO_2$) of aluminum ($AlO_2$), phosphorus ($PO_2$) and at least one additional element EL ($ELO_2$) have been disclosed for use in catalysts. In particular, such catalysts containing framework magnesium and designated MgAPSO-31 have demonstrated utility in the isomerization of $C_8$ aromatics.

The xylenes, para-xylene, meta-xylene and ortho-xylene, are important intermediates which find wide and varied application in chemical syntheses. Para-xylene upon oxidation yields terephthalic acid which is used in the manufacture of synthetic textile fibers and resins. Meta-xylene is used in the manufacture of products such as plasticizers, azo dyes, and wood preservers. Ortho-xylene is feedstock for phthalic anhydride production.

Xylene isomers from catalytic reforming or other sources generally do not match demand proportions as chemical intermediates, and further comprise ethylbenzene which is difficult to separate or to convert. Para-xylene in particular is a major chemical intermediate with rapidly growing demand, but amounts to only 20-25% of a typical $C_8$-aromatics stream. Adjustment of isomer ratio to demand can be effected by combining xylene-isomer recovery, such as adsorption for para-xylene recovery, with isomerization to yield an additional quantity of the desired isomer. Isomerization converts a non-equilibrium mixture of the xylene isomers which is lean in the desired xylene isomer to a mixture approaching equilibrium concentrations.

Catalysts for isomerization of $C_8$ aromatics ordinarily are classified by the manner of processing ethylbenzene associated with the xylene isomers. Ethylbenzene is not easily isomerized to xylenes, but it normally is converted in the isomerization unit because separation from the xylenes by superfractionation or adsorption is very expensive. A widely used approach is to dealkylate ethylbenzene to form principally benzene while isomerizing xylenes to a near-equilibrium mixture. An alternative approach is to react the ethylbenzene to form a xylene mixture in the presence of a solid acid catalyst with a hydrogenation-dehydrogenation function. The former approach commonly results in higher ethylbenzene conversion, thus lowering the quantity of recycle to the para-xylene recovery unit and concomitant processing costs, but the latter approach enhances xylene yield by forming xylenes from ethylbenzene. A catalytic composition and process which enhance conversion according to the latter approach, i.e., achieves ethylbenzene isomerization to xylenes with high conversion, is particularly advantageous.

SUMMARY OF THE INVENTION

A principal object of the present invention is to provide a novel molecular sieve which is useful for the conversion of hydrocarbons. More specifically, this invention is directed to a catalytic composition comprising a novel molecular sieve and a process for the isomerization of a mixture of xylenes and ethylbenzene resulting in improved yields and/or reduced processing costs.

This invention is based on the discovery that a MgAPSO-31 molecular sieve having a particular composition, configuration and X-Ray Diffraction Index as a measure of crystallinity provides a surprising effect in hydrocarbon-conversion activity. Accordingly, a broad embodiment of the invention is a hydrocarbon-conversion process which comprises contacting a hydrocarbon feedstock, in a hydrocarbon-conversion zone at hydrocarbon-conversion conditions, with a catalytic composition comprising a MgAPSO-31 molecular sieve which contains from about 0.003 to 0.011 mol fraction of magnesium in the microporous crystalline framework structure, demonstrates an XRDI of at least about 0.7, and comprises crystals with a median diameter of no more than about 1.0 micron and a median length along the c-axis of no more than about 3 microns, to obtain a converted product.

Preferably the MgAPSO sieve demonstrates at least about 0.8 XRDI.

The MgAPSO-31 molecular sieve favorably contains from about 0.005 to 0.008 mol fraction of magnesium in the microporous crystalline framework structure.

An alternative embodiment of the invention utilizes a pitted MgAPSO-31 molecular sieve which contains from about 0.003 to 0.011 mol fraction of magnesium in the microporous crystalline framework.

A more specific embodiment is a process for the isomerization of a non-equilibrium $C_8$-aromatic mixture of xylenes and ethylbenzene comprising contacting the mixture, in the presence of hydrogen in an isomerization zone at alkylaromatic-isomerization conditions, with a catalytic composition comprising at least one platinum-group metal component and MgAPSO-31 molecular sieve which contains from about 0.003 to 0.011 mol fraction of magnesium in the microporous crystalline framework structure, demonstrates an XRDI of at least about 0.7, and comprises crystals with a median diameter of no more than about 1.0 micron and a median length along the c-axis of no more than about 3 microns, to obtain an isomerized product.

In a yet more specific embodiment, the invention comprises a process for the isomerization of a non-equilibrium $C_8$-aromatic mixture of xylenes and ethylbenzene comprising contacting the mixture sequentially in first and second isomerization zones at respective first and second isomerization conditions with two catalysts, respectively comprising a first catalyst comprising a zeolitic aluminosilicate and a second catalytic composition comprising a MgAPSO-31 molecular sieve which contains from about 0.003 to 0.011 mol fraction of magnesium in the microporous crystalline framework structure, demonstrates an XRDI of at least about 0.7, and comprises crystals with a median diameter of no more than about 1.0 micron and a median length along the c-axis of no more than about 3 microns, to obtain an isomerized product.

These as well as other objects and embodiments will become evident from the following detailed description of the invention.

DETAILED DESCRIPTION OF THE INVENTION

Figure 1:
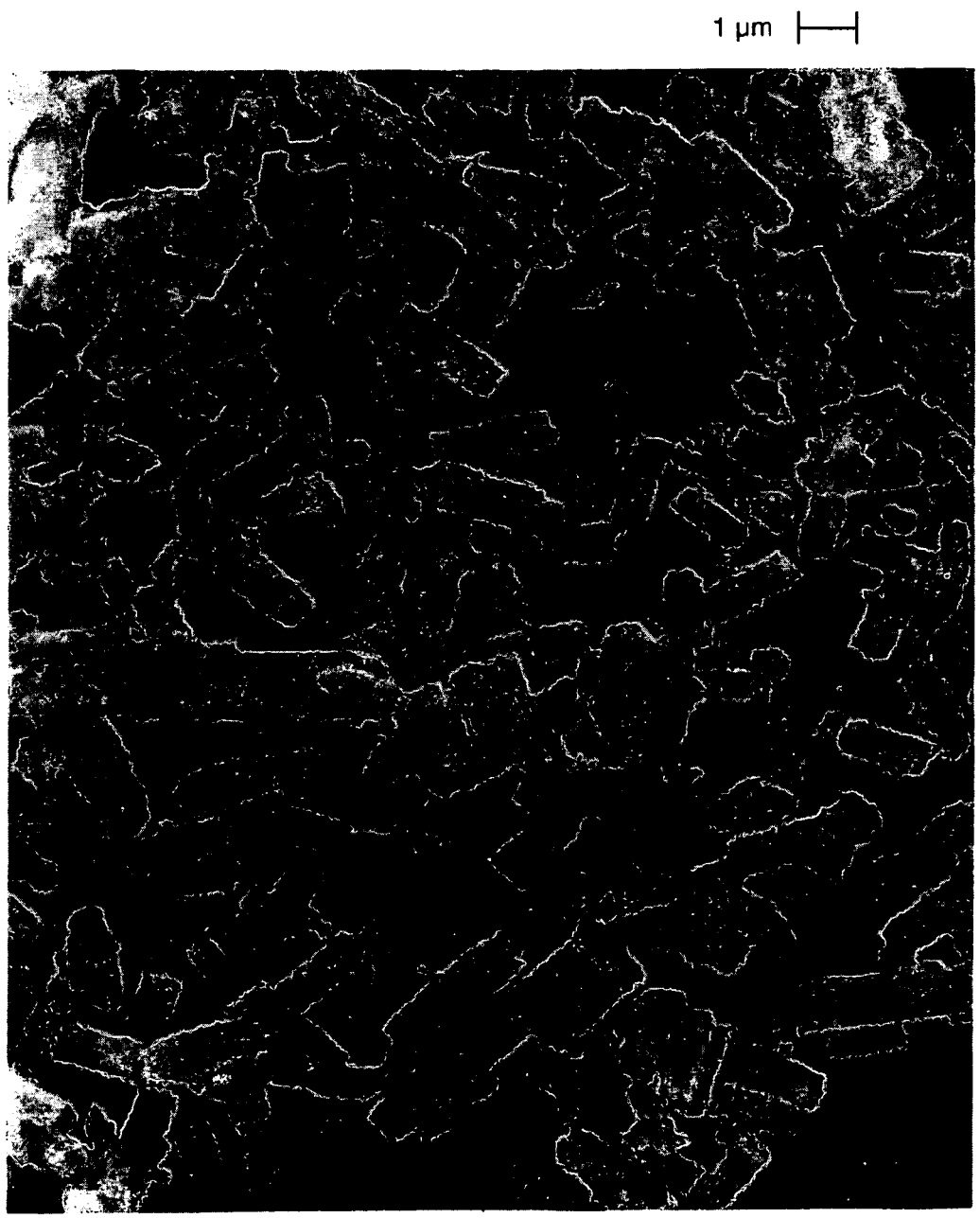
FIG. 1 is a scanning electron micrograph of a sieve of the invention.

As mentioned above, this invention is drawn to a MgAPSO-31 molecular sieve having a particular crystalline structure. The MgAPSO-31 molecular sieve of the invention can be understood by reference to the disclosure of U.S. Pat. No. 4,758,419, incorporated herein by reference thereto sieves have a microporous crystalline framework structure of $MgO_2^{-2}$, $AlO_2^-$, $PO_2^+$, and $SiO_2$ tetrahedral units having an empirical chemical composition on an anhydrous basis expressed by the formula:

$$mR: (Mg_wAl_xP_ySi_z)O_2$$

wherein "R" represents at least one organic templating agent present in the intracrystalline pore system; "m" represents the molar amount of "R" present per mole of $(Mg_w Al_x P_y Si_z)O_2$ and has a value of zero to about 0.3; and "w", "x", "y" and "z" represent the mole fractions of element magnesium, aluminum, phosphorus and silicon, respectively, present as tetrahedral oxides. The mole fraction of each framework constituent of the molecular sieve is defined as a compositional value which is plotted in phase diagrams of U.S. Pat. No. 4,758,419. The mole fractions "w", "x", "y" and "z" are generally defined as being within the limiting compositional values or points as follows:

| Point | Mole Fraction | | |
|-------|------|------|---------|
|       | x    | y    | (z + w) |
| A     | 0.60 | 0.38 | 0.02    |
| B     | 0.39 | 0.59 | 0.02    |
| C     | 0.01 | 0.60 | 0.39    |
| D     | 0.01 | 0.01 | 0.98    |
| E     | 0.60 | 0.01 | 0.39    |

It is an essential aspect of the present invention that the magnesium content of the MgAPSO-31 sieve of the invention is controlled within narrow limits. Specifically, the mole fraction "w" of framework magnesium in the molecular sieves of the invention is between about 0.003 and 0.011. Best results are obtained when the mol fraction of framework magnesium is between about 0.005 and 0.008. The MgAPSO-31 molecular sieve of the invention has a characteristic X-ray powder diffraction pattern which contains at least the d-spacings set forth below. For relative intensities in the table below w stands for weak, m for medium, s for strong, vs for very strong.

| 2Θ          | d             | Relative Intensity |
|-------------|---------------|--------------------|
| 8.4-9.501   | 10.53-9.3084  | w-s                |
| 20.2-20.4   | 4.40-4.35     | m                  |
| 22.0-22.1   | 4.04-4.022    | m                  |
| 22.5-22.7   | 3.952-3.92    | vs                 |
| 23.15-23.35 | 2.831-2.814   | w-m                |

MgAPSO sieves generally are synthesized by hydrothermal crystallization from an aqueous reaction mixture containing reactive sources of magnesium, silicon, aluminum and phosphorus and an organic templating agent for an effective time at effective conditions of pressure and temperature.

The organic templating agent, if any, can be selected from among those disclosed in U.S. Pat. No. 4,758,419. Generally this agent will contain one or more elements selected from Group VA (IUPAC 15) of the Periodic Table [See Cotton and Wilkinson, Advanced Inorganic Chemistry, John Wiley & Sons (Sixth Edition, 1999)], preferably nitrogen or phosphorus and especially nitrogen, and at least one alkyl or aryl group having from 1 to 8 carbon atoms. Preferred compounds include the amines and the quaternary phosphonium and quaternary ammonium compounds. Mono-, di- and tri-amines are advantageously utilized, either alone or in combination with a quaternary ammonium compound. Especially preferred amines include di-isopropylamine, di-n-propylamine, triethylamine and ethylbutylamine.

The reactive source of silicon may be silica, either as a silica sol or as fumed silica, a reactive solid amorphous precipitated silica, silica gel, alkoxides of silicon, silicic acid or alkali metal silicate and mixtures thereof.

The most suitable reactive source of phosphorus yet found for the instant process is phosphoric acid, but organic phosphates such as triethyl phosphate have been found satisfactory, and so also have crystalline or amorphous aluminophosphates such as the $AlPO_4$ composition of U.S. Pat. No. 4,310,440. Organo-phosphorus compounds selected as templating agents do not, apparently, serve as reactive sources of phosphorus, but these compounds may be transformed in situ to a reactive source of phosphorus under suitable process conditions.

The preferred aluminum source is either an aluminum alkoxide, such as aluminum tri-isopropoxide, or a pseudo-boehmite such as Versal. The crystalline or amorphous aluminophosphates which are a suitable source of phosphorus also are suitable sources of aluminum. Other sources of aluminum used in zeolite synthesis, such as gibbsite, sodium aluminate and aluminum trichloride, can be employed but are not preferred.

The reactive source of magnesium can be introduced into the reaction system in any form which permits the formation in situ of a reactive form of magnesium, i.e., reactive to form the framework tetrahedral unit $MgO_2^-2$. Compounds of magnesium which may be employed include oxides, hydroxides, alkoxides, nitrates, sulfates, halides, carboxylates (e.g. acetates and the like), organo-metallics and mixtures thereof.

Crystallization generally is effected in a sealed pressure vessel, preferably lined with an inert plastic material such as polytetrafluoroethylene. While not essential in general to the synthesis of MgAPSO compositions, stirring or other moderate agitation of the reaction mixture and/or seeding the reaction mixture with seed crystals of either the MgAPSO species to be produced or a topologically similar aluminophosphate, aluminosilicate or other molecular sieve composition facilitates the crystallization procedure. The reaction mixture is maintained advantageously under autogenous pressure at a temperature between 50° and 250° C., and preferably between 100° and 200° C., for a period of several hours to several weeks. The crystallization period advantageously will be between about 3 hours and 20 days. The MgAPSO-31 product is recovered by any convenient method such as centrifugation or filtration.

The criticality of crystallite size is believed to relate to the conversion of ethylbenzene in the isomerization process being pore-diffusion-limited rather than surface-reaction limited, although such theory in not intended in any way to limit the invention. The critical dimensions of the crystallites of the invention may be realized in any manner which is effective to reduce and control crystallite size and/or pitting. Preferable methods include high-speed stirring during crystallization to achieve high mass-transfer rates, higher solids in the reaction mixture, control of temperature and residence time of the reactants, and use of suitable templates. Larger crystallites may be milled to obtain smaller sizes, although this method is not preferred due to the range of sizes effected and possible structural damage.

Optimally the MgAPSO-31 product comprises small crystallites, which favor high ethylbenzene conversion in a process isomerizing $C_8$ aromatics as demonstrated in the examples. Preferably the crystallites have a median diameter, measured by scanning electron microscopy (SEM), of not more than about 1 micron. There is little benefit and considerable effort in reducing crystallite diameter below about 0.5 micron, i.e., preferred crystallite diameter is from about 0.5 to 1 micron. Median crystallite length along the direction of the pores of the sieve, designated the c-axis, is no more than about 3 microns.

The crystallinity of the sieves is an important aspect of the invention. X-Ray Diffraction Index ("XRDI") is a measure of relative crystallinity, and is a calculation of the ratio of the area under three designated XRD peaks of MgAPSO-31 divided by the area under three peaks of NIST-certified alpha-alumina as described below in more detail in Example 1. The MgAPSO-31 sieve of the invention has an XRDI of at least 0.7 and preferably 0.8.

After crystallization the MgAPSO-31 product may be isolated and advantageously washed with water and dried in air. The as-synthesized MgAPSO-31 will typically contain within its internal pore system at least one form of any templating agent, also referred to herein as the "organic moiety", employed in its formation. Most commonly the organic moiety is present, at least in part, as a charge-balancing cation. In some cases, the MgAPSO-31 pores are sufficiently large and the organic molecule sufficiently small that the removal of the latter may be effected by conventional desorption procedures. Generally, however, the organic moiety is an occluded molecular species which is too large to move freely through the pore system of the MgAPSO-31 product and must be thermally degraded and removed by calcining at temperatures, determined as sufficiently high to decompose and oxidize the template without removing elements from the framework, usually within the range of from 200° to 700° C.

It is within the scope of the invention that a catalytic composition prepared from the MgAPSO-31 of the invention comprises one or more additional non-zeolitic molecular sieves. Preferably the non-zeolitic molecular sieves are as a multi-compositional, multi-phase composite having contiguous phases, a common crystalline framework structure and exhibiting a distinct heterogeneity in composition, especially wherein one phase comprises a deposition substrate upon which another phase is deposited as an outer layer. Such composites are described in U.S. Pat. No. 4,861,739, incorporated herein by reference thereto. Suitable non-zeolitic molecular sieves include but are not limited to those of U.S. Pat. Nos. 4,440,871; 567,029 and 4,793,984, incorporated by reference.

A catalytic composition preferably is prepared by combining the molecular sieves of the invention with a binder for convenient formation of catalyst particles. The binder should be a porous, adsorptive support having a surface area of about 25 to about 500 $m^2/g$, uniform in composition and relatively refractory to the conditions utilized in the hydrocarbon conversion process. The term "uniform in composition" denotes a support which is unlayered, has no concentration gradients of the species inherent to its composition, and is completely homogeneous in composition. Thus, if the support is a mixture of two or more refractory materials, the relative amounts of these materials will be constant and uniform throughout the entire support. It is intended to include within the scope of the present invention carrier materials which have traditionally been utilized in hydrocarbon conversion catalysts such as: (1) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, etc.; (2) ceramics, porcelain, bauxite; (3) silica or silica gel, silicon carbide, clays and silicates including those synthetically prepared and naturally occurring, which may or may not be acid treated, for example attapulgus clay, diatomaceous earth, fuller's earth, kaolin, kieselguhr, etc.; (4) crystalline zeolitic aluminosilicates, either naturally occurring or synthetically prepared such as FAU, MEL, MFI, MOR, MTW (IUPAC Commission on Zeolite Nomenclature), in hydrogen form or in a form which has been exchanged with metal cations, (5) spinels such as $MgAl_2O_4$, $FeAl_2O_4$, $ZnAl_2O_4$, $CaAl_2O_4$, and other like compounds having the formula $MO-Al_2O_3$ where M is a metal having a valence of 2; and (6) combinations of materials from one or more of these groups.

The preferred binders for use in the present invention are refractory inorganic oxides, with best results obtained with a binder comprising alumina. Suitable aluminas are the crystalline aluminas known as the gamma-, eta-, and theta-aluminas. Excellent results are obtained with a matrix of substantially pure gamma-alumina. In addition, in some embodiments, the alumina matrix may contain minor proportions of other well known refractory inorganic oxides such as silica, zirconia, magnesia, etc. Whichever type of matrix is employed, it may be activated prior to use by one or more treatments including but not limited to drying, calcination, and steaming.

Using techniques commonly known to those skilled in the art, the catalytic composition of the instant invention may be composited and shaped into any useful form such as spheres, pills, cakes, extrudates, powders, granules, tablets, etc., and utilized in any desired size. These shapes may be prepared utilizing any known forming operations including spray drying, tabletting, spherizing, extrusion, and nodulizing.

A preferred form for the catalyst composite is an extrudate. The well-known extrusion method initially involves mixing of the non-zeolitic molecular sieve, either before or after adding metallic components, with the binder and a suitable peptizing agent to form a homogeneous dough or thick paste having the correct moisture content to allow for the formation of extrudates with acceptable integrity to withstand direct calcination. Extrudability is determined from an analysis of the moisture content of the dough, with a moisture content in the range of from 30 to 50 wt. % being preferred. The dough then is extruded through a die pierced with multiple holes and the spaghetti-shaped extrudate is cut to form particles in accordance with techniques well known in the art. A multitude of different extrudate shapes are possible, including, but not limited to, cylinders, cloverleaf, dumbbell and symmetrical and asymmetrical polylobates. One preferred extrudate shape is a trilobe. It is also within the scope of this invention that the extrudates may be further shaped to any desired form, such as spheres, by any means known to the art.

An alternative shape of the composite is a sphere, continuously manufactured by the well-known oil drop method. Preferably, this method involves dropping the mixture of molecular sieve, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50°-200° C. and subjected to a calcination procedure at a temperature of about 450°-700° C. for a period of about 1 to about 20 hours. This treatment effects conversion of the hydrogel to the corresponding alumina matrix.

A preferred component of the present catalytic composition is a platinum-group metal including one or more of platinum, palladium, rhodium, ruthenium, osmium, and iridium. The preferred platinum-group metal is platinum. The platinum-group metal component may exist within the final catalyst composite as a compound such as an oxide, sulfide, halide, oxysulfide, etc., or as an elemental metal or in combination with one or more other ingredients of the catalytic composition. It is believed that the best results are obtained when substantially all the platinum-group metal component exists in a reduced state. The platinum-group metal component generally comprises from about 0.01 to about 2 mass % of the final catalytic composite, calculated on an elemental basis.

The platinum-group metal component may be incorporated into the catalyst composite in any suitable manner. The preferred method of preparing the catalyst normally involves the utilization of a water-soluble, decomposable compound of a platinum-group metal to impregnate the calcined zeolite/binder composite. For example, the platinum-group metal component may be added to the calcined hydrogel by commingling the calcined composite with an aqueous solution of chloroplatinic or chloropalladic acid.

It is within the scope of the present invention that the catalytic composition may contain other metal components known to modify the effect of the platinum-group metal component. Such metal modifiers may include rhenium, tin, germanium, lead, cobalt, nickel, indium, gallium, zinc, uranium, dysprosium, thallium, and mixtures thereof. Catalytically effective amounts of such metal modifiers may be incorporated into the catalyst by any means known in the art.

The catalytic composition of the present invention may contain a halogen component. The halogen component may be fluorine, chlorine, bromine or iodine or mixtures thereof. Chlorine is the preferred halogen component. The halogen component is generally present in a combined state with the inorganic-oxide support. The halogen component is preferably well dispersed throughout the catalyst and may comprise from more than 0.2 to about 15 wt. %, calculated on an elemental basis, of the final catalyst. The halogen component may be incorporated in the catalytic composition in any suitable manner, either during the preparation of the inorganic-oxide support or before, while or after other catalytic components are incorporated.

The catalyst composite is dried at a temperature of from about 100° to about 320° C. for a period of from about 2 to about 24 or more hours and calcined at a temperature of from 400° to about 650° C. in an air atmosphere for a period of from about 0.1 to about 10 hours until the metallic compounds present are converted substantially to the oxide form. The optional halogen component may be adjusted by including a halogen or halogen-containing compound in the air atmosphere.

The resultant calcined composite may be subjected to a substantially water-free reduction step to insure a uniform and finely divided dispersion of the optional metallic components. Preferably, substantially pure and dry hydrogen (i.e., less than 20 vol. ppm $H_2O$) is used as the reducing agent in this step. The reducing agent contacts the catalyst at conditions, including a temperature of from about 200° to about 650° C. and for a period of from about 0.5 to about 10 hours, effective to reduce substantially all of the Group VIII metal component to the metallic state.

The resulting reduced catalytic composite may, in some cases, be beneficially subjected to a presulfiding operation designed to incorporate in the catalytic composite from about 0.05 to about 0.5 mass % sulfur calculated on an elemental basis. Preferably, this presulfiding treatment takes place in the presence of hydrogen and a suitable sulfur-containing compound such as hydrogen sulfide, lower molecular weight mercaptans, organic sulfides, etc. Typically, this procedure comprises treating the reduced catalyst with a sulfiding gas such as a mixture of hydrogen and hydrogen sulfide having about 10 moles of hydrogen per mole of hydrogen sulfide at conditions sufficient to effect the desired incorporation of sulfur, generally including a temperature ranging from about 10° up to about 600° C. or more. It is generally a good practice to perform this presulfiding step operation under substantially water-free conditions.

MgAPSO-31 sieves of the invention are useful for the conversion of hydrocarbons to obtain a convened product. The sieves preferably are utilized in combination with at least one inorganic-oxide matrix and one or more metals as described herein. A hydrocarbon feedstock is converted at hydrocarbon-conversion conditions including a pressure of about atmospheric to 200 atmospheres, temperatures of about 50° to 600° C., liquid hourly space velocities of from about 0.1 to 100 $hr^{-1}$, and, if hydrogen is present, hydrogen-to-hydrocarbon molar ratios of from about 0.01 to 80. Hydrocarbon-conversion processes which could advantageously employ catalytic compositions containing the MgAPSO-31 sieves of the invention include isomerization, reforming, dehydrocyclization, dehydrogenation, disproportionation, transalkylation, dealkylation, alkylation, polymerization, hydrocracking and catalytic cracking.

A particularly advantageous use for the MgAPSO-31 sieves of the invention is in the isomerization of isomerizable alkylaromatic hydrocarbons of the general formula $C_6H_{(6-n)}R_n$, where n is an integer from 2 to 5 and R is $CH_3$, $C_2H_5$, $C_3H_7$, or $C_4H_9$, in any combination and including all the isomers thereof to obtain more valuable isomers of the alkylaromatic. Suitable alkylaromatic hydrocarbons include, for example, ortho-xylene, meta-xylene, para-xylene, ethylbenzene, ethyltoluenes, trimethylbenzenes, diethylbenzenes, triethylbenzenes, methylpropylbenzenes, ethylpropylbenzenes, diisopropylbenzenes, and mixtures thereof.

Isomerization of a non-equilibrium $C_8$-aromatic mixture comprising ethylbenzene and xylenes is a particularly preferred application of the MgAPSO-31 sieves of the invention. Generally such mixture will have an ethylbenzene content in the approximate range of 5 to 50 mass %, an ortho-xylene content in the approximate range of 0 to 35 mass %, a meta-xylene content in the approximate range of 20 to 95 mass % and a para-xylene content in the approximate range of 0 to 15 mass %. It is preferred that the aforementioned $C_8$ aromatics comprise a non-equilibrium mixture, i.e., at least one $C_8$-aromatic isomer is present in a concentration that differs substantially from the equilibrium concentration at isomerization conditions. Usually the non-equilibrium mixture is prepared by removal of para- and/or ortho-xylene from a fresh $C_8$ aromatic mixture obtained from an aromatics-production process.

The alkylaromatic hydrocarbons may be utilized in the present invention as found in appropriate fractions from various refinery petroleum streams, e.g., as individual components or as certain boiling-range fractions obtained by the selective fractionation and distillation of catalytically cracked or reformed hydrocarbons. The isomerizable aromatic hydrocarbons need not be concentrated, but may be present in minor quantities in various streams. The process of this invention allows the isomerization of alkylaromatic-containing streams such as catalytic reformate with or without subsequent aromatics extraction to produce specified xylene isomers, particularly para-xylene. A $C_8$-aromatics feed to the present process may contain non-aromatic hydrocarbons, i.e., naphthenes and paraffins, in an amount up to 30 mass %.

According to the process of the present invention, an alkylaromatic hydrocarbon charge stock, preferably a non-equilibrium mixture of $C_8$ aromatics, and preferably in admixture with hydrogen, is contacted with a catalyst of the type hereinabove described in an alkylaromatic-hydrocarbon isomerization zone. Contacting may be effected using the catalyst in a fixed-bed system, a moving-bed system, a fluidized-bed system, or in a batch-type operation. In view of the danger of attrition loss of the valuable catalyst and of the simpler operation, it is preferred to use a fixed-bed system. In this system, a hydrogen-rich gas and the charge stock are preheated by suitable heating means to the desired reaction temperature and then passed into an isomerization zone containing a fixed bed of catalyst. The conversion zone may be one or more separate reactors with suitable means therebetween to ensure that the desired isomerization temperature is maintained at the entrance to each zone. The reactants may be contacted with the catalyst bed in either upward-, downward-, or radial-flow fashion, and the reactants may be in the liquid phase, a mixed liquid-vapor phase, or a vapor phase when contacted with the catalyst.

The alkylaromatic charge stock is contacted with the hereinbefore-described catalytic combination as in an isomerization zone while maintaining the zone at appropriate alkylaromatic-isomerization conditions. The conditions comprise a temperature ranging from about 0° to 600° C. or more, and preferably in the range of from about 300° to 500° C. The pressure generally is from about 1 to 100 atmospheres absolute, preferably less than about 50 atmospheres. Sufficient catalyst is contained in the isomerization zone to provide a liquid hourly space velocity of charge stock of from about 0.1 to 30 $hr^{-1}$, and preferably 0.5 to 10 $hr^{-1}$. The hydrocarbon charge stock optimally is reacted in admixture with hydrogen at a hydrogen/hydrocarbon mole ratio of about 0.01 to about 25 or more. Other inert diluents such as nitrogen, argon and light hydrocarbons may be present, and water may be added to the charge stock in an amount of from about 1 to about 1000 mass-ppm (parts per million).

It is within the scope of the invention that the alkylaromatic-hydrocarbon charge stock is contacted with two or more catalysts in each of two or more alkylaromatic-hydrocarbon isomerization zones. In this system, the feed mixture in the presence or absence of a hydrogen-rich gas are preheated by suitable heating means to desired reaction temperatures and then passed into isomerization zones containing fixed beds of two or more catalysts. This embodiment may comprise a single reactor or two or more separate reactors with suitable means therebetween to ensure that the desired isomerization temperature is maintained at the entrance to each zone. The two or more catalysts thus may be contained in separate reactors, arranged sequentially in the same reactor, mixed physically, or composited as a single catalyst. Each reactor may contain a catalyst bed in either upward-, downward-, or radial-flow fashion, and the reactants may be in the liquid phase, a mixed liquid-vapor phase, or a vapor phase when contacted with each catalyst. First and second isomerization conditions in each of the zones may comprise a temperature ranging from about 0° to 600° C. or more, and preferably in the range of from about 300° to 500° C.; a pressure generally from about 1 to 100 atmospheres absolute, preferably less than about 50 atmospheres; a liquid hourly space velocity of from about 0.1 to 30 $hr^{-1}$, and preferably 0.5 to 10 $hr^{-1}$; and hydrogen if present at a hydrogen/hydrocarbon mole ratio of about 0 to about 25 or more.

The two or more catalysts may comprise two catalysts of the present invention as described herein or one catalyst of the invention and one or more selected from the group consisting of other non-zeolitic molecular-sieves and zeolitic aluminosilicates. Preferably the catalysts are arranged in sequence, with the feed first contacting a zeolitic-aluminosilicate catalyst in a first isomerization zone to isomerize xylenes, optionally in the absence of hydrogen, and contacting effluent from the first zone with a catalyst of the present invention in a second isomerization zone to isomerize ethylbenzene to increase the para-xylene content of the product. Alternatively, the feed first contacts the catalyst of the present invention and then a zeolitic catalyst to obtain the isomerized product. Further details of an isomerization process comprising two or more catalysts are disclosed in U.S. Pat. No. 6,576,581 B1, incorporated herein by reference thereto.

The particular scheme employed to recover an isomerized product from the effluent of the reactors of the isomerization zone is not deemed to be critical to the instant invention, and any effective recovery scheme known in the art may be used. Typically, the reactor effluent will be condensed and the hydrogen and light-hydrocarbon components removed therefrom by flash separation. The condensed liquid product then is fractionated to remove light and/or heavy byproducts and obtain the isomerized product. In some instances, certain product species such as ortho-xylene may be recovered from the isomerized product by selective fractionation. The product from isomerization of $C_8$ aromatics usually is processed to selectively recover the para-xylene isomer by one or more of adsorption, crystallization or membrane separation as is known in the art. The isomerized product usually is combined with fresh feed for para-xylene recovery from both streams. Selective adsorption is preferred using crystalline aluminosilicates according to U.S. Pat. No. 3,201,491. Improvements and alternatives within the preferred adsorption recovery process are described in U.S. Pat. Nos. 3,626,020, 3,696,107, 4,039,599, 4,184,943, 4,381,419 and 4,402,832, incorporated herein by reference thereto.

It is within the scope of the invention that the isomerized product contains a greater-than-equilibrium concentration of para-xylene, i.e., the ethylbenzene is converted selectively to para-xylene such that the content of para-xylene in the product exceeds that which would be obtained by conventional xylene isomerization. This effect can be obtained specifically in a two-catalyst process in which conventional xylene isomerization precedes isomerization using a catalyst of the present invention.

In a separation/isomerization process combination relating to the processing of an ethylbenzene/xylene mixture, a fresh $C_8$-aromatic feed is combined with isomerized product comprising $C_8$ aromatics and naphthenes from the isomerization reaction zone and fed to a para-xylene separation zone; the para-xylene-depleted stream comprising a non-equilibrium mixture of $C_8$ aromatics is fed to the isomerization reaction zone, where the $C_8$-aromatic isomers are isomerized to near-equilibrium levels to obtain the isomerized product. In this process scheme non-recovered $C_8$-aromatic isomers preferably are recycled to extinction until they are either converted to para-xylene or lost due to side-reactions. Ortho-xylene separation, preferably by fractionation, also may be effected on the fresh $C_8$-aromatic feed or isomerized product, or both in combination, prior to para-xylene separation.

The following examples are presented for purpose of illustration only and are not intended to limit the scope of the present invention as presented in the claims.

EXAMPLES

The examples illustrate the criticality of molecular-sieve magnesium content, crystallinity, crystallite size and configuration and demonstrate the utility of the catalyst for isomerization of $C_8$ aromatics. These data do not, however, limit the applicability of the present invention as described hereinabove.

Example 1

A MgAPSO-31 molecular sieve of the invention was prepared in order to examine its properties and performance in an isomerization process. An amount of 187.14 grams of 85% $H_3PO_4$ was combined with 600 grams of deionized water in a reaction vessel and placed in an ice bath. When the temperature of the solution reached below 20° C., 333.19 grams of aluminum tri-isopropoxide (AlP) was added slowly and blended with a Mueller mixer at 650 rpm until a homogeneous mixture was observed. Next, 46.66 grams of Ludox AS-40 (40% $SiO_2$) was added to the slurry. In a separate beaker 5.40 grams of magnesium acetate tetrahydrate was dissolved in 79 grams of water; the solution was added to the slurry and blended to form a homogeneous mixture. The organic template dipropylamine (148 grams) was added to the mixture followed by 2.8 grams of $AlPO_4$-31 seed, and the resulting slurry was blended until a homogeneous mixture was observed. The final mixture was heated to 195° C. for 12 hours to effect crystallization at 500 rpm and autogenous pressure. After cooling to room temperature, the product slurry was removed from the reaction vessel and centrifuged to recover solids which were washed and dried.

The properties of the recovered solids were determined as follows:

| | |
|---|---|
| 100 Mg/T (mole % Mg in tetrahedral oxides) | 0.8 |
| 100 Si/T (mole % Si in tetrahedral oxides) | 1.5 |
| 100 Al/T (mole % Al in tetrahedral oxides) | 49.2 |
| 100 P/T (mole % P in tetrahedral oxides) | 48.5 |
| XRDI (relative crystallinity) | 1.00 |
| Diameter of crystal, microns (median) | 0.6 |
| Length of crystal, microns (median) | 1.7 |

X-Ray Diffraction Index ("XRDI") is a measure of relative crystallinity, and is a calculation of the ratio of the area under three designated XRD peaks of MgAPSO-31 divided by the area under three peaks of NIST-certified alpha-alumina. The MgAPSO sieve of the invention has an XRDI of at least 0.7 and preferably 0.8. For calculation of the relative X-ray intensity for MgAPSO-31, the following procedure is used. The data are collected using Cu Kα radiation with a step time of 1 sec/step and a step width of 0.01 degrees. Alpha-alumina NBS 674a is used as primary standard and integrated absolute intensity data are collected for the peaks in the 2θ ranges: 24.6-26.6, 34.2-36.2, and 42.4-44.4, which correspond to the indices (012), (104), and (113), respectively. The integrated absolute intensities of the MgAPSO-31 peaks in the ranges 20.0-20.5 and 21.7-23.0, corresponding to the indices (021), (3-11), and (410), are collected under the same conditions. The XRDI of the MgAPSO-31 is calculated by dividing the absolute intensity of the sample by the absolute intensity of the alpha alumina.

The length of the crystal was determined as being along a "c-axis" parallel to the long axis of the crystal. For this determination a transmission electron microscopy (TEM) sample was prepared by dispersing powder in isopropyl alcohol and placing a droplet of the suspension on a thin carbon film (holey carbon supported by a copper grid). The electron diffraction was done on a 3000F TEM at 300 kV accelerating voltage. For indexing the patterns the structure published by Bennett and Kirchner, Zeolites 12, 338 (1992) was used (ATO framework structure). This has a rhombohedral unit cell, and the hexagonal representation was used for the indexing. In this cell the c-axis is the unique axis, and is perpendicular to the honeycomb-shaped basal plane. Several patterns from two typical rod-shaped crystals were indexed. By using the goniometer tilt settings as auxiliary information it was possible to obtain unique indexing of all patterns. The patterns and the relative orientation of the crystal (from images taken at the same settings) confirm the model of the c-axis being parallel to the long axis of the crystal.

Crystal dimensions were determined by scanning electron microscopy (SEM). Both for crystal diameter and crystal length the medians are reported.

FIG. 1 is a scanning electron micrograph of the Example 1 molecular sieve at 10 kV and a magnification of 10,000 times.

Additional examples were prepared in a manner similar to that of Example 1, and each of the samples were characterized as described above. The results were:

| | 100Mg, | 100Si, | 100Al, | 100P/T | XRDI | Diameter | Length |
|---|---|---|---|---|---|---|---|
| Example 1 | 0.8, | 1.5, | 49.2, | 48.5 | 1.00 | 0.6 | 1.7 |
| Example 2 | 0.7, | 1.1, | 48.7, | 49.4 | 1.00 | 0.9 | 3.1 |
| Example 3 | 1.0, | 1.9, | 48.9, | 48.2 | 1.00 | 0.9 | 2.7 |
| Example 4 | 1.1, | 2.0, | 48.0, | 49.0 | 0.94 | 0.6 | 1.5 |
| Example 5 | 0.8, | 1.5, | 49.2, | 48.5 | 1.03 | 0.7 | 1.8 |
| Example 6 | 0.4, | 2.3, | 49.6, | 47.8 | 0.88 | 0.5 | 1.6 |
| Example 7 | 0.4, | 2.1, | 48.8, | 48.8 | 1.06 | 0.7 | 2.7 |
| Example 8 | 0.3, | 1.5, | 48.8, | 49.4 | 0.84 | 0.6 | 1.7 |
| Example 9 | 0.3 | 2.2, | 49.4, | 48.1 | 1.08 | 1.6 | 6.3 |

The MgAPSO-31's in the examples described above were formed into cylindrical extrudates composited with 50 weight-% alumina binder and calcined at 675° C. In the following step they were impregnated with 0.3 weight-% platinum and then calcined and reduced at 566° C., followed by sulfidation using H2S. They were then tested for activity and selectivity in isomerizing ethylbenzene to xylenes. Tests were carried out at 690 kPa and 375° C. at weight hourly space velocities (WHSV) as indicated. The feedstock to the test unit contained either 18% or 14% ethylbenzene as indicated (composition in wt.-%):

|  | 18% EB Feed | 14% EB Feed |
| --- | --- | --- |
| Toluene | 0.2 | 0.2 |
| Ethylbenzene | 18.0 | 13.7 |
| Para-xylene | 17.3 | 18.4 |
| Meta-xylene | 40.4 | 42.2 |
| Ortho-xylene | 17.6 | 19.0 |
| $C_8$ naphthenes | 6.3 | 6.3 |
| $C_8$ paraffins | 0.1 | 0.1 |

Ethylbenzene conversion (EB Conv, %) was measured in each case, along with product para-xylene/xylene (PX/X, %) and $C_8$-ring loss (C8RL, %) across the reactor, as indicated below.

EB Conv, %=((EB/$C_8$ aromatics, % in feed)−(EB/C8 aromatics, % in product)/(EB/C8 aromatics, % in feed)

PX/X, %=(PX in product, %)/(Xylenes in product, %)

C8RL, %=(($C_8$ aromatic+naphthenic ring in feed, %)− ($C_8$ aromatic+naphthenic ring in product, %))/ ($C_8$ aromatic+naphthenic ring in feed, %)

For some catalyst examples, there are more than one set of testing results with two different feeds. The WHSV for tests done with 18% EB feed is in the range of 2.5-2.7. At similar WHSV the higher is the conversion the higher is the activity. C8 RL, on the other hand, generally increases with conversion due to increased severity. Accordingly, selectivity comparison between different catalyst examples is made at similar conversion levels. For some examples the EB conversion was fixed at 30% and the WHSV to obtain 30% conversion was reported. For this series, the higher is the WHSV the higher is the activity.

While catalysts in examples 1-8 were all prepared according to the invention here, they nevertheless show differences in performance due to their differences in Mg content, relative crystallinity and crystal size.

|  | WHSV | Feed EB, % | EB Conv, % | PX/X, % | C8RL, % |
| --- | --- | --- | --- | --- | --- |
| Example 1 | 2.7 | 18 | 50 | 25.0 | 2.8 |
|  | 5.0 | 14 | 30 | 24.2 | 1.2 |
| Example 2 | 2.7 | 18 | 47 | 25.0 | 2.3 |
| Example 3 | 2.5 | 18 | 46 | 25.0 | 2.4 |
| Example 4 | 2.5 | 18 | 45 | 25.3 | 1.8 |
| Example 5 | 2.7 | 18 | 46 | 25.7 | 1.3 |
|  | 4.4 | 14 | 30 | 24.4 | 1.0 |
| Example 6 | 2.5 | 18 | 35 | 25.6 | 1.1 |
|  | 2.7 | 14 | 30 | 24.5 | 0.9 |
| Example 7 | 2.5 | 18 | 35 | 24.8 | 2.3 |
| Example 8 | 2.5 | 18 | 40 | 25.4 | 1.3 |
|  | 3.5 | 14 | 30 | 24.5 | 0.8 |
| Example 9 | 1.7 | 14 | 30 | 24.5 | 1.0 |

From the comparison above of characteristics and performances, it is apparent that there is an interaction among magnesium content, relative crystallinity and crystal dimensions. An effective MgAPSO-31 molecular sieve contains from about 0.003 to 0.011 mol fraction of magnesium in the microporous crystalline framework structure, demonstrates at least about 0.80 relative x-ray crystallinity, and comprises crystals having a median diameter of no more than about 1.0 micron and a median length along the c-axis of no more than about 3 microns. Mg is a critical element for MgAPSO-31 activity, however, too much Mg increases C8RL. Preferably, the content of magnesium in the microporous crystalline framework structure of the molecular sieve is from about 0.005 to 0.008 mol fraction. Generally, the higher the crystallinity and the smaller the crystal size the better is the performance.

Comparing performances with 18% EB feed, examples 1-5 produced very high activity, with conversions in the 45-50% range. On the other hand, again with 18% EB feed, examples 6-8, produced results at the lower end of the desired activity range. Without being bound by any theory, it is noteworthy to mention that catalysts in examples 6-8 had either less than the optimal level of Mg and/or not so high relative crystallinity. Results with 14% EB feed were consistent with 18% EB feed results. Again examples 1 and 5 produced very high activity, while examples 6 and 8 produced activity in the lower end of the desired range. Catalyst from example 9 had crystals that were too long and not prepared according to the invention. Accordingly example 9 produced undesirably low activity.

Figure 2:
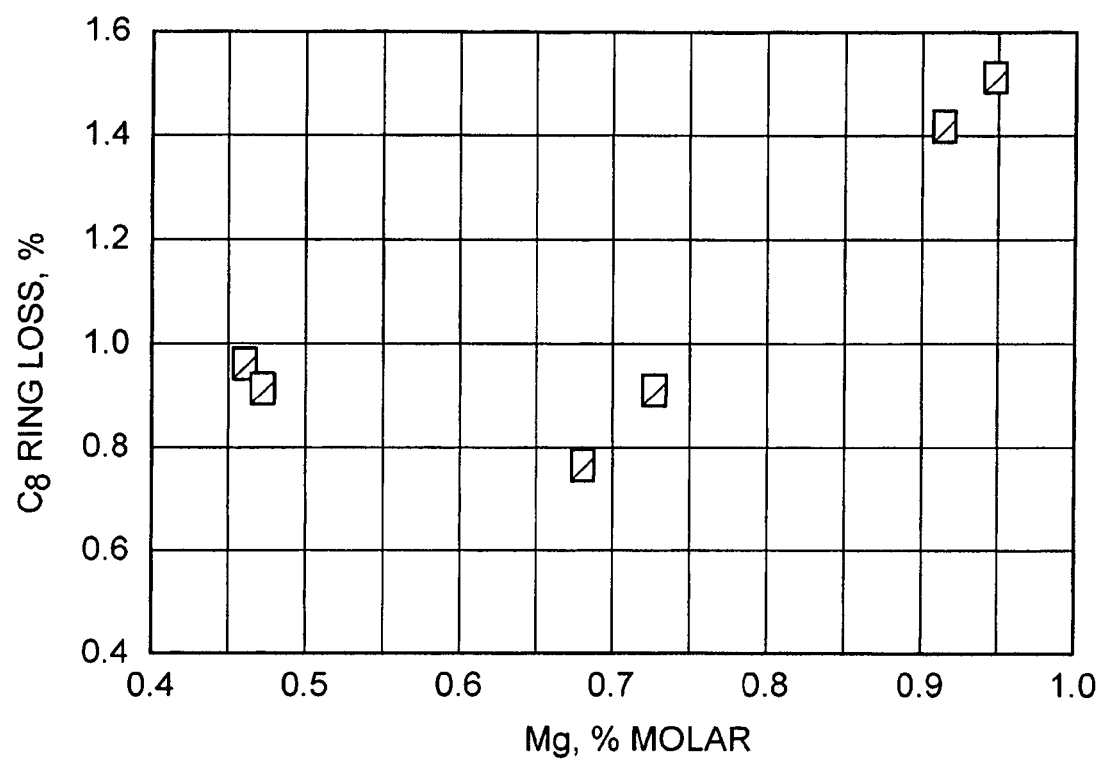
FIG. 2 is a graph of ring loss against sieve magnesium content.

Further tests were carried out to determine the effect of magnesium content on C8-ring loss. Another group of sieves were composited with 50 weight-% alumina binder and calcined at 600° C. to form trilobes. The catalysts were then impregnated with 0.3 weight-% platinum, calcined and reduced at 566° C. and finally sulfided with H2S. Tests were carried out at 690 kPa and 364° C. with a feed containing 14% ethylbenzene to effect 30% ethylbenzene conversion. The results are plotted in FIG. 2, and show that C8-ring loss is lowest with around 0.7 mole-% magnesium in the sieve framework and higher magnesium levels cause an increase in C8RL.

Further examination of examples 1-9 also reveals the interaction of Mg content and crystal size for effecting selectivity. Again without being bound by any theory, example 5 with smaller crystals and lower Mg, when tested using 18% EB feed, resulted in 1.3% C8RL at 46% conversion, while example 3 with larger crystals and higher Mg resulted in 2.4% C8RL at 46% conversion. Example 6 with smaller crystals, again when tested with 18% EB feed, resulted in 1.1 % C8RL at 35% EB conversion, while example 7 with larger crystals resulted in 2.3% C8RL at 35% EB conversion.

Example 10

A MgAPSO-31 molecular sieve was prepared using pseudoboehmite hydrated alumina (Versal) rather than AlP in order to examine its properties and performance in an isomerization process. An amount of 152.1 grams of Versal 250 was added slowly into a blend of 237.6 grams of 85% $H_3PO_4$ in 700 grams of deionized water in a reaction vessel and blended with a Mueller mixer at 650 rpm to effect a homogeneous mixture. Next, 58.7 grams of Ludox AS-40 (40% $SiO_2$) was added and mixed into the slurry. In a separate beaker 6.6 grams of magnesium acetate tetrahydrate was dissolved in 54.6 grams of water; the solution was added to the slurry and blended to form a homogeneous mixture. The organic template dipropylamine (187.7 grams) was added to the mixture followed by 2.8 grams of $AlPO_4$-31 seed, and the resulting slurry was blended until a homogeneous mixture was observed. The final mixture was heated to 195° C. for 12 hours to effect crystallization at 500 rpm and autogenous pressure. After cooling to room temperature, the product slurry was removed from the reaction vessel and centrifuged to recover solids which were washed and dried.

The properties of the recovered solids were determined as follows in the same manner as for Example 1:

| | |
|---|---|
| 100 Mg/T | 1.0 |
| 100 Si/T | 8.7 |
| 100 Al/T | 48.9 |
| 100 P/T | 41.3 |
| RI | 0.69 |
| Diameter of crystal, microns | 0.9 |
| Length of crystal, microns | 2.0 |

Additional examples were prepared in a manner similar to that of Example 10, and each of the samples was characterized as described above. The results were:

| | 100 Mg, | 100 Si, | 100 Al, | 100 P/T | XRDI | Diameter | Length |
|---|---|---|---|---|---|---|---|
| Example 10 | 1.1, | 8.7, | 48.9, | 41.3 | 0.69 | 0.9 | 2.0 |
| Example 11 | 1.3, | 5.2, | 48.7, | 44.8 | 0.90 | 1.0 | 3.8 |
| Example 12 | 0.8, | 5.6, | 49.3, | 44.4 | 0.75 | 1.0 | 4.0 |
| Example 13 | 1.7, | 5.1, | 48.3, | 44.9 | 0.77 | 1.0 | 4.4 |
| Example 14 | 1.0, | 6.8, | 49.0, | 43.3 | 0.60 | 1.0 | 3.6 |

The examples described above were tested for activity and selectivity in isomerizing ethylbenzene to xylenes. The sieves were composited with 50 weight-% alumina binder and calcined at 675° C. The catalysts were then impregnated with 0.3 weight-% platinum, calcined and reduced at 566° C. and then sulfided. Tests were carried out at 690 kPa and 375° C. at weight hourly space velocities (WHSV) as indicated. The feedstock to the test unit contained 18% ethylbenzene. Ethylbenzene conversion (EB Conv) was measured in each case, along with product para-xylene/xylene (PX/X) and $C_8$-ring loss (C8RL) as indicated.

| | % EB feed | WHSV | EB Conv, % | PX/X, % | C8RL, % |
|---|---|---|---|---|---|
| Example 10 | 18 | 2.7 | 33 | 25.0 | 1.2 |
| Example 11 | 18 | 2.7 | 35 | 25.0 | 1.7 |
| Example 12 | 18 | 2.5 | 42 | 25.2 | 2.0 |
| Example 13 | 18 | 2.7 | 26 | 24.8 | 1.3 |
| Example 14 | 18 | 2.7 | 17 | 24.3 | 0.7 |

Examples 10-14 were not prepared according to the invention. Without being bound by any theory, example 10 produced low activity due to low relative crystallinity, while examples 11 and 13 produced low activity due to large crystals and finally example 14 produced low activity due to both low relative crystallinity and large crystals.

Example 12, though not prepared according to invention, produced high activity due to the pitted nature of the crystals. Pitting occurs in MgAPSO-31 crystals due to retrograde solubility, causing partial dissolution of crystals during cooling, following the crystallization at 195° C.

Figure 3:
FIG. 3 is a scanning electron micrograph of a pitted sieve.

FIG. 3 is a scanning electron micrograph (SEM) of the Example 12 molecular sieve at 10 kV and a magnification of 10,000 times. Note the pitted nature of the crystals compared to those of Example 1; the mesopore volume is 0.165 cc/gram for Example 12 compared to 0.043 cc/gram for Example 1. It is believed that the presence of pitting may be detected by enhanced mesopore volume and by broader XRD peaks and may enhance performance.

The invention claimed is:

1. A hydrocarbon-conversion process selected from isomerization, reforming, dehydrocyclization, dehydrogenation, disproportionation, transalkylation, dealkylation, polymerization, hydrocracking, and catalytic cracking, which comprises contacting a hydrocarbon feedstock, in a hydrocarbon-conversion zone at hydrocarbon-conversion conditions for isomerization, reforming, dehydrocyclization, dehydrogenation, disproportionation, transalkylation, dealkylation, polymerization, hydrocracking, and catalytic cracking, with a catalytic composition comprising a MgAPSO-31 molecular sieve which contains from about 0.005 to 0.008 mol fraction of magnesium in the microporous crystalline framework structure, demonstrates an XRDI of at least about 0.8, and comprises crystals with a median diameter of no more than about 1.0 micron and a median length along the c-axis of no more than about 3 microns, to obtain a converted product, optionally a platinum-group metal component, and optionally an inorganic-oxide binder.

2. The process of claim 1 wherein the composition comprises a platinum-group metal component.

3. The process of claim 2 wherein the platinum-group metal component comprises from about 0.1 to 5 mass % platinum on an elemental basis.

4. The process of claim 1 wherein the composition comprises an inorganic-oxide binder.

5. The process of claim 4 wherein the inorganic-oxide binder comprises alumina.

6. A process for the isomerization of a non-equilibrium $C_8$-aromatic mixture of xylenes and ethylbenzene comprising contacting the mixture, in the presence of hydrogen in an isomerization zone at alkylaromatic-isomerization conditions, with a catalytic composition comprising at least one platinum-group metal component and MgAPSO-31 molecular sieve which contains from about 0.005 to 0.008 mol fraction of magnesium in the microporous crystalline framework structure, demonstrates an XRDI of at least about 0.8, and comprises crystals with a median diameter of no more than about 1.0 micron and a median length along the c-axis of no more than about 3 microns, to obtain an isomerized product.

7. The process of claim 6 wherein the isomerization conditions comprise a temperature ranging from a temperature ranging from about 0° to 600°, a pressure generally from about 1 to 100 atmospheres absolute, a liquid hourly space velocity of from about 0.1 to 30 $hr^{-1}$, and a hydrogen/hydrocarbon mole ratio of about 0.01 to about 25.

8. The process of claim 6 further comprising addition of water to the charge stock in an amount of from about 1 to about 1000 mass-ppm.

9. The process of claim 6 wherein the composition further comprises a platinum-group metal component.

10. The process of claim 6 wherein the composition further comprises an inorganic-oxide binder.

11. The process of claim 6 further comprising recovering ortho-xylene from one or both of the isomerized product and fresh $C_8$-aromatic feed.

12. The process of claim 6 further comprising selectively recovering para-xylene from the isomerized product and a fresh $C_8$-aromatic feed.

13. The process of claim 6 wherein the isomerized product comprises a greater-than-equilibrium concentration of para-xylene.

14. A process for the isomerization of a non-equilibrium $C_8$-aromatic mixture of xylenes and ethylbenzene comprising contacting the mixture sequentially in first and second isomerization zones at respective first and second isomerization conditions with two catalysts respectively comprising:
   (a) a first catalyst comprising a zeolitic aluminosilicate; and,
   (b) a second catalytic composition comprising a MgAPSO-31 molecular sieve which contains from about 0.003 to 0.011 mol fraction of magnesium in the microporous crystalline framework structure, demonstrates an XRDI of at least about 0.7, and comprises crystals with a median diameter of no more than about 1.0 micron and a median length along the c-axis of no more than about 3 microns, to obtain an isomerized product.

15. The process of claim 14 wherein each of first and second isomerization conditions in each respective zone comprise a temperature ranging from about 0° to 600°, a pressure generally from about 1 to 100 atmospheres absolute, a liquid hourly space velocity of from about 0.1 to 30 $hr^{-1}$, and a hydrogen/hydrocarbon mole ratio of from about 0 to about 25 or more.

16. The process of claim 14 wherein the isomerized product comprises a greater-than-equilibrium concentration of para-xylene.

* * * * *